US008624599B2

(12) United States Patent
Kamlowski et al.

(10) Patent No.: US 8,624,599 B2
(45) Date of Patent: Jan. 7, 2014

(54) ANALYSIS SYSTEM WITH GPC AND NMR SPECTROSCOPY COUPLING, IN PARTICULAR FOR THE ANALYSIS OF SAMPLES HAVING POLYMERS

(75) Inventors: Andreas Kamlowski, Karlsruhe (DE); Thorsten Hofe, Bechtolsheim (DE); Markus Cudaj, Karlsruhe (DE); Manfred Wilhelm, Weingarten (DE); Gisela Guthausen, Rheinstetten (DE)

(73) Assignees: Bruker BioSpin GmbH, Rheinstetten (DE); PSS Polymer Standards Service GmbH, Mainz (DE); Karlsruher Institut fuer Technologie, Karlsruhe (DE)

( * ) Notice: Subject to any disclaimer, the term of this patent is extended or adjusted under 35 U.S.C. 154(b) by 391 days.

(21) Appl. No.: 12/929,748

(22) Filed: Feb. 14, 2011

(65) Prior Publication Data
US 2011/0204894 A1 Aug. 25, 2011

(30) Foreign Application Priority Data
Feb. 24, 2010 (DE) .......................... 10 2010 002 316

(51) Int. Cl.
*G01V 3/00* (2006.01)
(52) U.S. Cl.
USPC ........................................................ 324/321
(58) Field of Classification Search
USPC ................................................. 324/300–322
See application file for complete search history.

(56) References Cited

U.S. PATENT DOCUMENTS

| 7,554,736 | B2 * | 6/2009 | Ohta et al. ..................... 359/581 |
| 7,741,433 | B2 * | 6/2010 | Pollock et al. ................ 530/300 |
| 7,868,102 | B2 * | 1/2011 | Moriyama et al. ............ 525/540 |
| 8,071,676 | B2 * | 12/2011 | Matsuda et al. .............. 524/572 |
| 8,324,403 | B2 * | 12/2012 | Yabe et al. ..................... 548/440 |
| 2004/0241871 | A1 * | 12/2004 | Shinoda et al. ............... 436/161 |
| 2005/0075479 | A1 | 4/2005 | Blackbourn et al. |

FOREIGN PATENT DOCUMENTS

GB 2 367 664 B 5/2004

OTHER PUBLICATIONS

Alison Nordon, Colin A. McGill and David Littlejohn "Process NMR spectrometry", Analyst, 2001, 126, 260-272.
Tatsuki Kitayama and Koichi Ute "On-line Coupling of LC and NMR", Graham A. Webb (ed.) Modern Magnetic Resonance, 395-401. © 2006 Springer.
Klaus Albert "On-line use of NMR detection in separation chemistry", Journal of Chromatography A, 703 (1995) 123-147.

(Continued)

*Primary Examiner* — Dixomara Vargas
(74) *Attorney, Agent, or Firm* — Paul Vincent (57) ABSTRACT

An analysis system (1) for the analysis of a sample, comprises a gel permeation chromatograph (14) that is coupled with a nuclear magnetic resonance (=NMR) spectrometer. The chromatograph (14) has a gel permeation chromatography (=GPC) separating column system (6a) that is filled with porous particles (21). The NMR spectrometer is configured as a low-field NMR spectrometer (8) with a permanent magnet system (9) for generating a $B_0$ field of the NMR spectrometer. The low-field NMR spectrometer (8) comprises a shim system (10) with which homogeneity of the $B_0$ field of at least 0.5 ppm can be achieved in a right circular cylindrical sample volume (27) having a diameter of at least 5 mm and a length of at least 15 mm. The system permits the quantitative and qualitative chemical analysis of samples containing substances of different molecular size using a less expensive apparatus.

23 Claims, 7 Drawing Sheets

(56) References Cited

OTHER PUBLICATIONS

Noriyuki Watanabe and Eiji Niki "Direct-Coupling of FT-NMR to High Performance Liquid Chromatography", 194, Proc. Japan Acad., 54, Ser. B (1978).

Ernst Bayer, Klaus Albert, Michael Nieder and Edgar Grom "On-line Coupling of High-Performance Liquid Chromatography and Nuclear Magnetic Resonance", Journal of Chromatography, 186 (1979) 497-507.

* cited by examiner

ANALYSIS SYSTEM WITH GPC AND NMR SPECTROSCOPY COUPLING, IN PARTICULAR FOR THE ANALYSIS OF SAMPLES HAVING POLYMERS

This application claims Paris Convention priority of DE 10 2010 002 316.7 filed Feb. 24, 2010 the complete disclosure of which is hereby incorporated by reference.

BACKGROUND OF THE INVENTION

The invention relates to an analysis system for the analysis of a sample, comprising a gel permeation chromatograph that is coupled with a nuclear magnetic resonance (=NMR) spectrometer, wherein the chromatograph has a gel permeation chromatography (=GPC) separating column that is filled with porous particles.

Such an analysis system is described, for example, in A. Nordon at al., Analyst (2001), No. 126, pp. 260-272.

The analysis and monitoring of the polymer quality, particularly with respect to molecule size, chain length distribution, molecular linking, and chemical composition is a basic requirement for the development and production of powerful polymers, composite materials containing polymers and macromolecules. Measuring methods are used in the monitoring of the polymer quality that must be both selective with respect to molecular size and sensitive to the chemical composition.

The measuring methods for monitoring polymer quality are largely based on liquid-chromatography separation methods, in particular, gel permeation chromatography (=GPC), also called size exclusion chromatography (=SEC) or GPC/SEC. The substance to be examined (usually a mixture of macromolecules of different sizes) is dissolved in an eluent (eluting agent) and passes through a separating column that contains a stationary phase; the stationary phase delays the progress of the various macromolecules in the sample for different lengths of time. In GPC, the macromolecules contained in the sample are separated according to size (hydrodynamic radius). In this case, the separation effect of GPC is based on entropic interaction with the stationary phase and therefore provides no information about the chemical composition of the macromolecules. In other chromatography methods such as high performance liquid chromatography (=HPLC), on the other hand, the separation effect is based on enthalpic interaction.

The actual chemical analysis of the sample can be performed with one of the spectrometers placed downstream of the chromatographic separation. Isolated spectrometers would only provide averaged information about the chemical composition of the molecular blend contained in the sample; information about individual fractions of the molecular blend can only be derived after upstream separation.

Currently, mainly ultraviolet (=UV) spectrometers and infrared (=IR) spectrometers are used in conjunction with GPC. UV and IR spectrometers are attractively priced but their measurement capability is limited for physical reasons, so that both the qualitative and quantitative information they can provide about the chemical composition of the sample both is rather limited.

Currently, the most powerful method of chemical analysis of samples containing polymers in general use is high-resolution, high field NMR spectroscopy using superconducting magnets (corresponding to a proton frequency of typically 500 MHz or more). High-field NMR spectroscopy, usually implemented as FT-NMR, is currently the most versatile and precise method of identifying chemical substances. However, even with high-field NMR spectroscopy, complete chemical deformulation of all components of a sample containing a polymer blend can only be achieved with upstream separation.

The coupling of GPC and high-field NMR is, for example, summarized in a review by T. Kitayama, K. Ute, "On-line SEC-NMR," in "Modern Magnetic Resonance," pp. 395-401, edited by G. A. Webb, 2006.

However, the use of high-field NMR spectroscopy coupled with GPC requires a very large investment in apparatus. The high-field NMR spectrometer used for the qualitative and quantitative chemical analysis of fractions is very expensive to procure and maintain, in particular, due to the use of superconducting magnet coils, which are difficult to manufacture and usually large and heavy, and the need to cool them with expensive liquid helium during operation. The handling of cryogenic liquids and the complex measuring methods and complicated operation also mean they are difficult and expensive to operate.

Where individual quality control and process monitoring tasks have to be performed, low-field NMR spectrometers are often used. Commercially available low-field NMR devices such as "the minispec" from Bruker Optics GmbH, Ettlingen, Germany, are based on permanent magnet systems and are considerably smaller and more economical than high-field NMR devices. However, as a rule, they only allow little to no dispersion, so that chemical differentiation and identification of the components of samples by means of chemical shift is hardly possible.

A. Nordon et al., Analyst (2001), No. 126, pp 260-272, in their review describe the possibilities of low-field NMR in online use. This is where the reference to spectroscopic measurements in the low field is also to be found. In the summary, it is also pointed out that methods of high-field NMR, as are used, for example, at 500 MHz in conjunction with GPC coupling, could be of interest for online NMR analysis.

The coupling of HPLC and NMR in the laboratory is also known; see, for example, K. Albert J. Chromatography A, No. 703 (1995), pp. 123-147. Here, electromagnets for field generation are used, cf. N. Watanabe, E. Niki, Proc. Japan. Acad. 54, Ser. B, 194 (1978), or also E. Bayer et al., J. Chromatography 186, pp. 497-507 (1979).

The object of this invention is to provide an analysis system with which quantitative and qualitative chemical analysis of samples containing substances of different molecular sizes can be performed with less expensive apparatus.

SUMMARY OF THE INVENTION

This object is solved by an analysis system of the type stated in the introduction, characterized in that the NMR spectrometer is constituted as a low-field NMR spectrometer with a permanent magnet system for the generation of a $B_0$ field of the NMR spectrometer, wherein the low-field NMR spectrometer comprises a shim system with which homogeneity of the $B_0$ field of 0.5 ppm or better, preferably 0.1 ppm or better, can be achieved in a right circular cylindrical sample volume with a diameter of at least 5 mm and a length of at least 15 mm, and wherein the low-field NMR spectrometer further comprises a lock function for compensating for a drift of the $B_0$ field, and wherein the chromatograph has a GPC separating column system that comprises at least the one GPC separating column, wherein all GPC separating columns of the GPC separating column system together have an internal volume of at least 45 $cm^3$, preferably at least 100 $cm^3$.

The inventors have discovered that even when the GPC is coupled with a low-field NMR spectrometer, comprehensive analysis of the samples containing polymers is possible, in particular, the chemical identification and quantification of repeat units of the polymer blends in the sample in correlation with the molecular weight distribution. However, for this, the analysis system requires several specific adaptations with regard to a shim and lock function in the low-field NMR spectrometer, and also adaptation of the GPC separating column, which is placed upstream of the low-field NMR spectrometer. By incorporating the inventive measures, sufficient sensitivity of the analysis system can be achieved so that polymer blends can be separated, individually identified, and quantified with respect to their composition. Despite the necessary adaptations, the inventive system permits much simpler and lower-cost analysis than the known coupling of GPC and high-field NMR.

The Low-Field NMR Spectrometer

The NMR spectrometer of the inventive analysis system is based on a permanent magnet system that produces the static $B_0$ field for the NMR measurement. Typically, the strength of the magnetic field generated by the permanent magnet system corresponds to a proton frequency of 2 to 60 MHz if the materials currently available for permanent magnets are used. Permanent magnet systems of strength 20 MHz to 50 MHz are preferably used for the purpose of this invention. The permanent magnet system is simply structured, low in maintenance, and economical to procure and maintain.

The permanent magnet system is complemented by a shim system that ensures homogeneity of 0.5 ppm or better in a volume with a length of at least 15 mm and a diameter of at least 5 mm. The range of the NMR spectrometer in which the required homogeneity is achieved is called the available sample volume within the scope of this invention (please note that the measuring cell of the NMR probe head in which the sample for the NMR measurement is placed should occupy a space within or equal to the sample volume). In conventional low-field NMR spectrometers, no comparable field homogenization is usually performed. The inventive increased homogeneity improves the resolution of chemical shifts and J-couplings. The shim system can have passive shim elements and/or electric shims. An electric shim can comprise a shim coil or a group of shim coils; an electric shim is typically used for separate setting of an individual development coefficient of the $B_0$ field. Preferably, at least 8, especially preferably, at least 12 electric shims are provided; in individual cases, fewer electric shims (approximately 3) are sufficient.

Further, the NMR spectrometer is inventively equipped with a lock function. The lock function can be implemented, in particular, a) by means of a separate channel, in particular, in the case of the $^1$H-NMR with a $^{19}$F reference probe, or b) in the software by means of an internal or external reference.

If a separate channel is used, a $B_0$ drift is typically produced by the direct correction of the $B_0$ field with an electrical $z^0$ shim. If the lock function is implemented in software, spectra are typically frequency-corrected directly (during acquisition) before summation of the scans according to the drift, and feedback is effected with respect to the spectrometer frequency. In some cases, it is also possible to initially store a large number of obtained spectra and perform a frequency correction later, for instance as part of a cross-correlation or a maximum search. With the lock function, the effect of the drift of the $B_0$ field, which can noticeably distort the measurement results of permanent magnet systems, can be compensated for.

The GPC Separating Column

The chromatograph (or the GPC separating column system) separates the components contained in the sample according to their hydrodynamic volume, and the downstream NMR spectrometer then allows analysis of the individual components, in particular, by means of chemical shift or J-coupling.

The gel permeation chromatograph comprises at least one sample dispenser, one pump, and one GPC separating column (separation stage). Additionally, in particular, a degassing device can be provided for the sample and/or the eluent. It is important to note that the sample comprises the substance to be measured (usually a polymer blend) and a solvent in which the substance to be measured is dissolved. The solvent and the eluent are preferably identical.

According to the invention, a GPC separating column system is provided, comprising one or more GPC separating columns connected in parallel. The structure of the GPC separating column has a considerably larger internal volume for the analysis of samples containing polymers than a conventional GPC separating column. The internal volume (interior), in which the stationary phase in the form of porous particles is contained, of inventively at least 45 cm$^3$ (distributed among one or more GPC separating columns) permits an enlarged sample injection quantity. This enlarged sample injection quantity can be used to put a larger volume of the measuring substance after chromatographic separation into the sample volume of the low-field NMR spectrometer, and thus to increase the concentration or absolute volume of the measuring substance in the sample volume. In this way, the signal-to-noise (=S/N) ratio of the NMR measurements of the measuring substance can be significantly improved.

If a single GPC separating column is used, it will typically have, for the purpose of this invention, an interior diameter (which determines the internal volume) of at least 15 mm (and a base area of at least approx. 2 cm$^2$), preferably at least 20 mm (and a base area of at least approx. 3 cm$^2$). It must be noted that the base area of the interior of a separating column is typically constituted as a circle; however, other base area shapes are possible. If multiple, parallel GPC separating columns are used, the base areas of the GPC columns are added together to form a sum SGFL, which is preferably at least approx. 1.5 cm$^2$, and especially preferably at least 3 cm$^2$.

Applications

The invention provides a modular, flexibly configurable analysis system (measuring system) for the chemically selective separation and identification of polymers and polymer blends, wherein the chemical selective identification is performed by means of low-field NMR spectroscopy, based on permanent magnet technology, the separation, on the other hand, is performed by means of GPC. The analysis system resulting from the coupling and optimization of the individual devices can be used across industries for the chemical analysis of polymers, e.g. for paints and varnishes, films, plastics and insulating materials, and for medical and pharmaceutical products in industrial production, processing and research and development, but also for the chemical analysis of biopolymers. Areas of application of the invention are, in particular, material receipt and product final inspection, production control and quality monitoring of polymers and biopolymer basic products and finished products. The inventive analysis system can be used, in particular, for the spectral separation and identification of industrial polymer and biopolymer-relevant aromatic, olefinic protons bound to oxygen, as well as aliphatic protons as a function of the molecular mass.

In a preferred embodiment of the inventive analysis system, the GPC separating column system comprises exactly one GPC separating column and the GPC separating column has an aspect ratio ASP=L/R of at least 5, preferably at least 15, L being the length of the separating segment of the GPC separating column in the flow direction and R being the radius equivalent of the cross-sectional area QFL of the interior of the GPC separating column perpendicular to the flow direction with $R=(QFL/\pi)^{1/2}$. A configuration with exactly one separating column is particularly easy to implement. The single separating column then has at least one internal volume of 45 cm$^3$ for the stationary phase (that is, the porous particles). The provided aspect ratios of the GPC separating column ensure a sufficient retention time difference between the individual fractions.

In an alternative, especially advantageous embodiment, the GPC separating column system comprises multiple GPC separating columns connected in parallel, in particular, wherein the GPC separating columns are connected via a diffuser. Large sample injection quantities can be separated in the parallel-connected separating columns, thus reducing running of the sample. The inventive internal volume of at least 45 cm$^3$ of the GPC separating column system, in which the stationary phase is disposed, is distributed among the parallel GPC separating columns so that relatively small diameters of the individual separating columns can be chosen. The parallel GPC separating columns are typically identical, including the particle filling. The optional diffuser compensates for input pressure differences and preferably also retention time differences, for example, resulting from manufacturing tolerances, between the parallel GPC separating columns. Where the separating segment is equally long in all the parallel GPC separating columns, an aspect ratio ASP=L/R can be determined for a radius equivalent that is calculated from the sum SGFL of the base areas of all the separating columns (perpendicular to the flow direction) according to $R=(SQFL/\pi)^{1/2}$, and with uniform length L of the separating segments of all separating columns (parallel to the flow direction), wherein the aspect ratio is preferably 5 or more, especially preferably 15 or more. For these aspect ratios a sufficient retention time difference of the individual fractions is ensured.

In a highly preferred embodiment of the inventive analysis system, at least 25%, preferably at least 50%, of the particles in the at least one GPC separating column have a diameter of at least 15 μm, preferably, at least 20 μm. In this invention, particle size distributions are preferably used in the stationary phase that have a high proportion of large particles with a diameter of 15 μm or more compared with conventional GPC separating columns. This reduces the flow resistance that the separating column or the separating column system exerts on the sample and the eluent. This reduction of the flow resistance also makes it possible to handle large sample injection quantities in the analysis system well and, in particular, fast. The high proportion of large particles, is in particular, preferred for fast flow rates (typically according to a linear flow of 2 cm/min and more, for molecules of >10$^6$ Da (Dalton) also 1 cm/min and more). It is important to note that, in accordance with the invention and in particular at slower flow rates (typically corresponding to a linear flow of 1 cm/min and less), particle size distributions with a high proportion of small particles can be favorably applied.

An embodiment in which the low-field NMR spectrometer comprises digital data acquisition with digital filters is also preferred.

In particular, an FIR filter (finite impulse response) can be used as a digital filter. The sensitivity of the NMR system can be increased with digital data acquisition and the use of digital filters.

An advantageous further development of this embodiment also includes an evaluation unit for applying numerical mathematical manipulations to increase the sensitivity and/or selectivity. In particular, convolution operations can be set up and applied as mathematical operations in the evaluation unit.

In a further advantageous embodiment, the analysis system comprises a sample that contains a deuterated solvent. If a deuterated solvent is used, practically no solvent signals occur with $^1$H-NMR.

An especially preferred embodiment provides a control unit that is shared by the chromatograph and the low-field NMR spectrometer. The common control facilitates adjustment of the processes and the control in the NMR spectrometer to the processes and/or control in the chromatograph. In particular, measuring processes in the NMR spectrometer can be started specifically when individual fractions from the chromatograph reach the NMR probe head. A common control can ensure a holistic (matched) procedure adapted to the sample type in the overall analysis system.

An advantageous further development of this embodiment provides a control unit that comprises a control library in which control parameters are stored for controlling the NMR spectrometer and the chromatograph for various types of samples and/or for various configurations of the chromatograph and/or for various probe heads of the NMR spectrometer. With the control library, a suitable measurement procedure for the analysis system can preferably be automatically determined (suggested) and preferably automatically executed (triggered) for the experiment at hand (for which at least the total concentration of the substance to be measured in the sample and the type of solvent in the sample should be defined). This makes the analysis system particularly user friendly. The control unit can also contain a data analysis function, which comprises NMR spectrum and model libraries.

Furthermore, an embodiment is advantageous in which the chromatograph comprises a temperature-controllable sample segment. In this way, the measuring conditions for certain sample types can be optimized, for example, to stabilize the physical properties of the sample, in particular, the solvent properties. Likewise, the measuring conditions can be kept sufficiently stable and reproducible for quantification. Preferably, the sample segment between the GPC separating column system and the sample volume in the probe head can be fully temperature-controlled.

In an especially preferred embodiment of the inventive analysis system, a further analytical measuring device, such as, for example, a concentration detector, in particular, a refractometer (=RI), infrared (=IR), ultraviolet (=UV), or refractive index detector, is disposed in a sample segment of the analysis system between the GPC separating column system of the chromatograph and a probe head of the NMR spectrometer and/or downstream of the probe head of the NMR spectrometer. With this additional analytical measuring device, a distinction between, and in particular, the beginning and the end of individual fractions along the sample segment downstream of the GPC separating column system can be determined. This information can be used, for example, to trigger the acquisition of NMR spectra.

Further, an embodiment is advantageous in which a polarization system is disposed in or along the sample segment of the analysis system upstream of the probe head of the NMR spectrometer. In this way, the NMR signal intensity can be increased. The polarization system can be integrated into the at least one separating column and/or in the region of a supply line to the probe head. A hyperpolarization system is based, for example, on light or microwave radiation with the addition of chemical substances. Prepolarization by means of an additional magnetic field along the flow segment is also possible (especially for low $B_0$ magnetic fields in the NMR detection range).

In an especially preferred embodiment, the analysis system further comprises an HPLC separating column. This configuration permits multidimensional chromatography, in particular SEC-LAC (=liquid adsorption chromatography) NMR. The HPLC separating column and the GPC separating column system are connected in series in any sequence, and the NMR spectrometer is connected downstream of the separating columns. As a rule, a store of multiple sample fractions is inserted between the separating columns of the HPLC and the GPC; a further store for multiple sample fractions can be connected downstream of the second separating stage. It is important to note that, according to this invention, the coupling of multidimensional chromatographic methods with the low-field NMR, for example, embodied as spectroscopy or relaxometry or diffusometry, is generally possible. Examples of such couplings are SEC-LCCC (=liquid chromatography at critical conditions of adsorption)-NMR or also SEC-TGIC (=temperature gradient interaction chromatography)-NMR, or also SEC-LAC coupling.

In an advantageous embodiment, a probe head of the NMR spectrometer
- is designed for a pressure of the probe head of at least 40 bar, preferably at least 60 bar,
- and/or has an RF quality (Q factor) of at least 100, preferably at least 140,
- and/or has a filling factor of at least 40%, preferably at least 60%,
- and/or has supply lines with an internal diameter of 0.4 mm or less, preferably 0.25 mm. An NMR probe head constructed in this way permits greater sensitivity of the NMR measurements. By using narrow supply lines, running of the sample (or one of its fractions) in the eluent will be reduced so that the separation is maintained and can, in particular, be detected by means of a downstream RI detector. However, the eluent and/or the sample must then be pumped through the supply lines with greater pressure. A correspondingly robust probe head will withstand this pressure and is preferably used within the scope of this invention.

Equally possible is an embodiment in which the low-field NMR spectrometer comprises a Q switch. The Q switch can be used, in particular, with solid-body-like (rapidly relaxing) signals to improve detection sensitivity.

The scope of this invention also comprises the use of an inventive analysis system for the analysis of samples containing polymers, in particular, for the chemical identification and quantification of the repeat units of the samples in correlation with the molecular weight distribution. With the inventive analysis system, the cost of the apparatus for the comprehensive analysis of samples containing polymers can be considerably reduced as compared with a GPC coupled with high-field NMR spectroscopy.

Equally part of the scope of this invention is a method for analyzing a sample, in particular, a sample containing polymers, wherein the sample is separated in a gel permeation chromatograph with a GPC separating column filled with porous particles and the fractions of the sample are examined in a coupled NMR spectrometer, characterized in that the NMR spectrometer is constituted as a low-field NMR spectrometer in which a permanent magnet system is used to generate a $B_0$ field of the NMR spectrometer, wherein a shim system is used in the low-field NMR spectrometer with which a homogeneity of the $B_0$ field of 0.5 ppm or better, preferably 0.1 ppm or better, is set in a right circular cylindrical sample volume with a diameter of at least 5 mm and a length of at least 15 mm, wherein a lock function for compensating for a drift of the $B_0$ field is further implemented in the low-field NMR spectrometer, and that, in order to separate the sample, a GPC separating column system comprising at least the one GPC separating column is implemented, wherein all GPC separating columns of the GPC separating column system together constitute an internal volume of at least 45 cm$^3$, preferably at least 100 cm$^3$. With the inventive method, a comprehensive analysis of a sample, in particular containing a polymer blend, can be performed at low cost. The inventive method or one of its variants can be performed with an inventive analysis device or one of its embodiments.

A variant of the inventive method is preferred in which the GPC separating column system used is a GPC separating column system that comprises exactly one GPC separating column, wherein the GPC separating column has an aspect ratio ASP=L/R of at least 5, preferably at least 15, L being length of the separating segment of the GPC separating column in the flow direction, R being radius equivalent of the cross-section area QFL of the interior of the GPC separating column perpendicular to the flow direction, wherein $R=(QFL/\pi)^{1/2}$. This variant is particularly simple.

Equally preferable is an alternative method variant in which a GPC separating column system comprising a plurality of GPC separating columns connected in parallel is used as the GPC separating column system, in particular, wherein the GPC separating columns are connected via a diffuser. In this variant, running of the sample in the eluent is minimized, in particular in the case of large sample injection quantities.

In a preferred variant of the inventive method, in at least the one GPC separating column, particles with a particle size distribution are used in which at least 25%, preferably at least 50%, of the particles have a diameter of at least 15 μm, preferably at least 20 μm. In this way, the flow resistance of the at least one GPC separating column can be reduced and the pressure in the analysis system thereby reduced (see above in this respect).

A method variant is preferred in which the analysis of the sample is performed with stopped flow or in continuous flow. In the stopped flow method, fractions of the sample can be collected, for example, in multi-port valves, and subsequently measured as a whole during a freely selectable dwell time in the NMR spectrometer, by which a better S/N ratio can be achieved and/or further experiments (1D and 2D) that result in improved identification can be performed. In continuous flow operation, the dwell time of the fractions in the NMR spectrometer is determined by the ongoing separation in the separating column system and the application of eluent; continuous flow operation can be implemented with simpler apparatus and often permits faster measurements.

In an equally preferred variant, the analysis of the sample in the NMR spectrometer comprises the spectral analysis and quantitative determination of $^1$H and/or of non-hydrogen X nuclei, especially wherein X is chosen to be $^{13}$C or $^{19}$F. As a rule, a larger chemical shift dispersion can be used for X nuclei than for H. Due to the inherently low NMR sensitivity of the X nuclei, preferably a stopped flow and/or NMR methods for increasing the sensitivity, for example, double resonance methods, are used here. In the case of $^{19}$F analyses, if necessary, the lock system is modified or a separate NMR probe head is used.

In a highly preferred method variant, the examination of the sample in the NMR spectrometer comprises the application of pulse sequences for suppressing the solvent, in particular, relaxation filters and/or frequency-selective pulse sequences and/or gradient-assisted NMR methods, and/or spectral resolution for the separation of the analytes and/or multivariate data analysis methods, in particular PLS (partial least square regression) or MCR (multivariate curve resolution) or FID-DECRA (free induction decay direct exponential curve resolution), and/or multi-pulse method for improving the S/N$\sqrt{t}$ ratio even in dynamic magnetization equilibrium. The proposed measures facilitate solvent suppression (especially the first measure), an improved quantitative analysis (second and third measures), an improved signal-to-noise (=S/N) ratio, and preservation of the spectral resolution (fourth measure).

Further advantages of the invention can be derived from the description and the drawing. According to the invention, the characteristics stated above and further explained below can also be used either individually or in any combination. The embodiments shown and described are not intended to be an exhaustive list but are examples used to explain the invention.

BRIEF DESCRIPTION OF THE DRAWING

The invention is depicted in the drawing and is explained in more detail by means of embodiments. The figures show.

DESCRIPTION OF THE PREFERRED EMBODIMENT

The invention relates to a device and method that permits the low-cost, fast and comprehensive chemical deformulation of, for example, complex polymer structures and polymer compounds. The inventive device comprises a two-stage analysis system, that is composed of a low-field NMR spectrometer and a gel permeation chromatograph (GPC) connected upstream; the GPC is also called SEC (size exclusion chromatography) or GPC/SEC. This makes selective separation with respect to molecule size and the chemical identification of the separated molecules possible in a single device. The user preferably communicates via a tailored interface that comprises both technologies.

By contrast with the coupling of GPC and high-field NMR known from prior art, in this invention, low-field NMR devices are used, which, in terms of procurement costs, operability and size as well as maintenance requirement and surrounding parameters are comparable to those of a gel permeation chromatograph. A further difference is the use of permanent magnet systems, which are very robust and resource-saving as compared with superconducting magnet systems.

Besides the coupling of the chromatograph and the NMR spectrometer by means a common flow segment, the invention also proposes measures for the control, data processing and for the user interface so that it can be deployed universally in laboratories and testing stations. As part of this invention, the components of the NMR spectroscopy and the GPC (SEC) are attuned to each other. The invention also permits modular and flexible configuration of the overall analysis system.

By specific measures, in particular, the use of a shim system, the application of a lock function and an adequately sized GPC separating system, sufficient sensitivity for a qualitative and quantitative chemical analysis of the composition of samples, in particular, those containing polymer blends, is achieved in the analysis system.

Explorative Measurement Results

Figure 1:
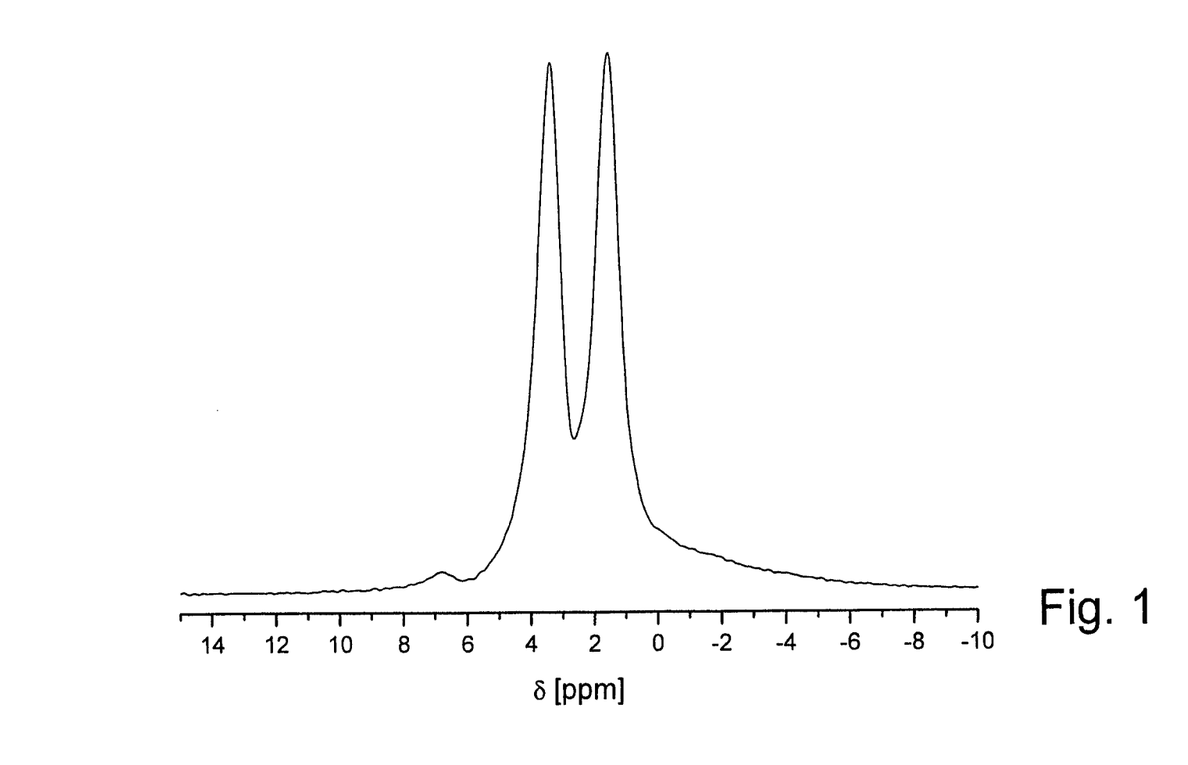
FIG. 1 A $^1$H FT-NMR spectrum of a polystyrene solution in $^1$H-THF, acquired with a low-field NMR spectrometer at 20 MHz.

FIG. 1 shows the spectrum of a polystyrene solution in $^1$H-THF, which was acquired in a continuous flow measurement at a flow rate of V=2 ml/min in a mq20 low-field NMR spectrometer with electric shims at 20 MHz without a GPC separating column system in the flow segment. The concentration of polystyrene (=PS) here was 20 g/l (22.5 mg PS/g THF). The two peaks of the solvent (tetrahydroflurane, THF) can be seen at 1.6 ppm and 3.4 ppm. The aromatic signal component of the polystyrene is detectable at 6.8 ppm. The much more intensive peak of the THF is superimposed on the aliphatic component, which can therefore not be seen. This figure demonstrates the feasibility of low-field spectroscopy.

Figure 2:
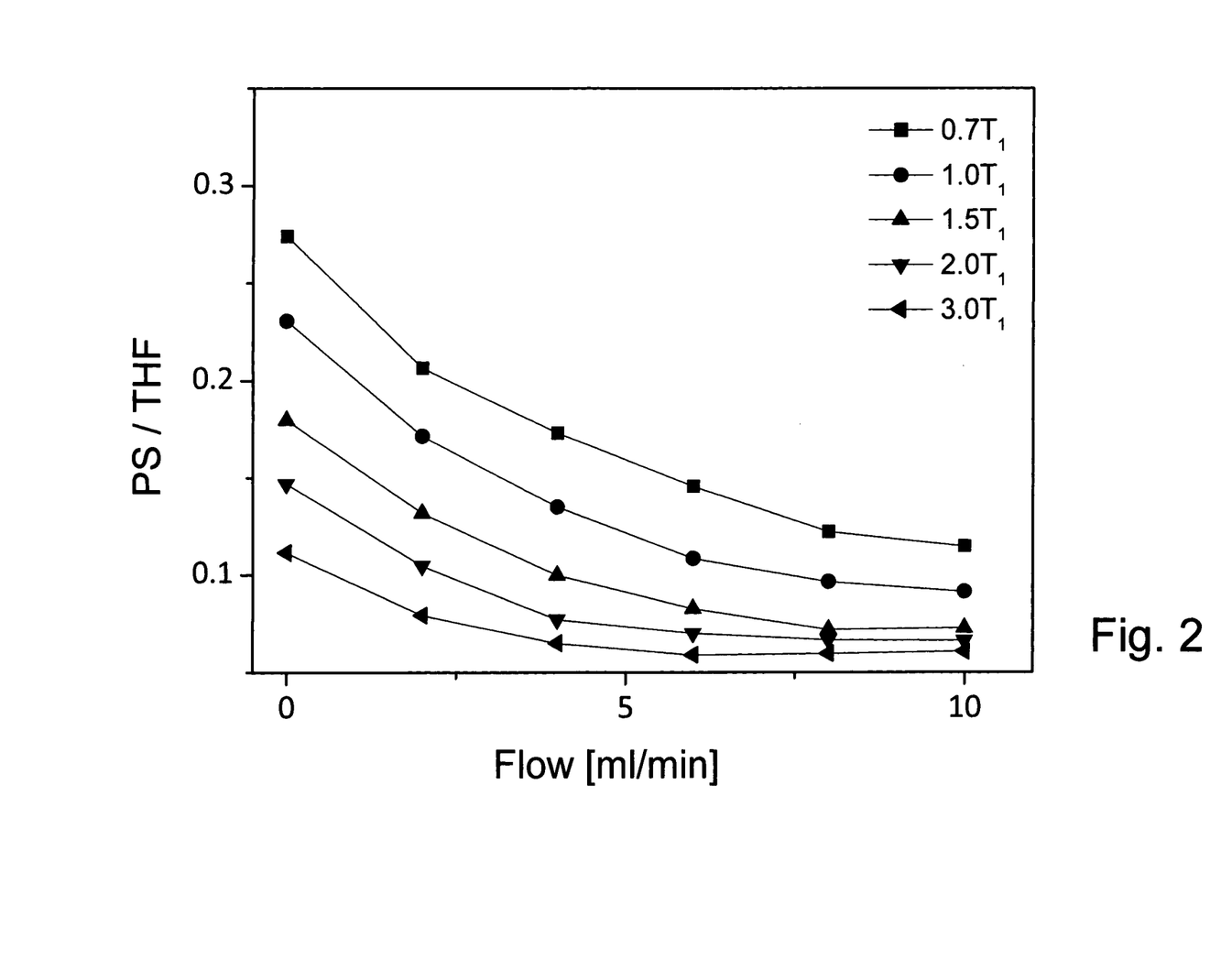
FIG. 2 A chart plotting the ratios of the NMR signal amplitudes of the aromatic component of polystyrene to those of the solvent THF as a function of the flow rate, at various repetition rates of the NMR experiment, also acquired at 20 MHz.

FIG. 2 shows a chart of the ratio of the signal amplitude of the aromatic component of polystyrene to that of the solvent THF as a function of the flow rate; the measurement was again performed at 20 MHz at an mq20 with electric shims. An implied parameter is the repetition rate of the single experiments, with reference to the relaxation time $T_1$ of the polystyrene. The figure shows that the ratio of the signal amplitudes can be shifted considerably toward the polystyrene, in particular, for small volume flows and short repetition rates. Further optimization can be achieved by selecting a suitable excitation pulse (flip angle). The example depicted in FIG. 2 shows that solvent suppression can be achieved in the low field by making use of the differing relaxation characteristics between the solvent and polymer sample.

Figure 3:
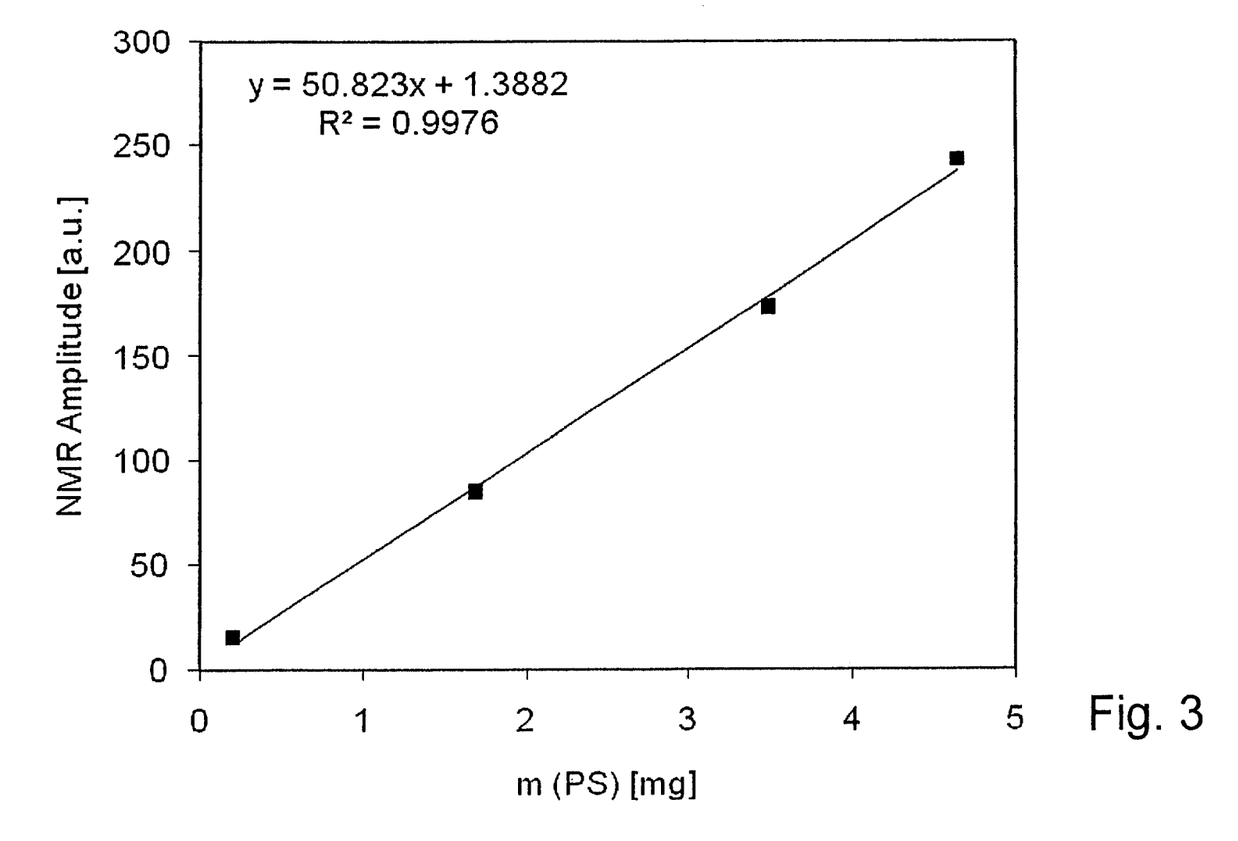
FIG. 3 A correlation diagram of the NMR signal amplitude of the aromatic component of polystyrene as a function of the initial mass of the sample, also acquired at 20 MHz.

FIG. 3 shows a correlation diagram: The signal amplitude of the aromatic polystyrene signal as a function of the initial mass of the polystyrene sample, again measured at 20 MHz. A linear correlation produces a squared correlation coefficient $R^2$=0.997 for the aromatic components. This demonstrates that the quantity can even be determined in the low field simply by ascertaining the amplitude.

The experimental results of FIGS. 1 to 3 were obtained on a Bruker "the minispec" system of the mq type, with an additional electric shim system.

Design of Embodiments of Inventive Analysis Systems

Figure 4:
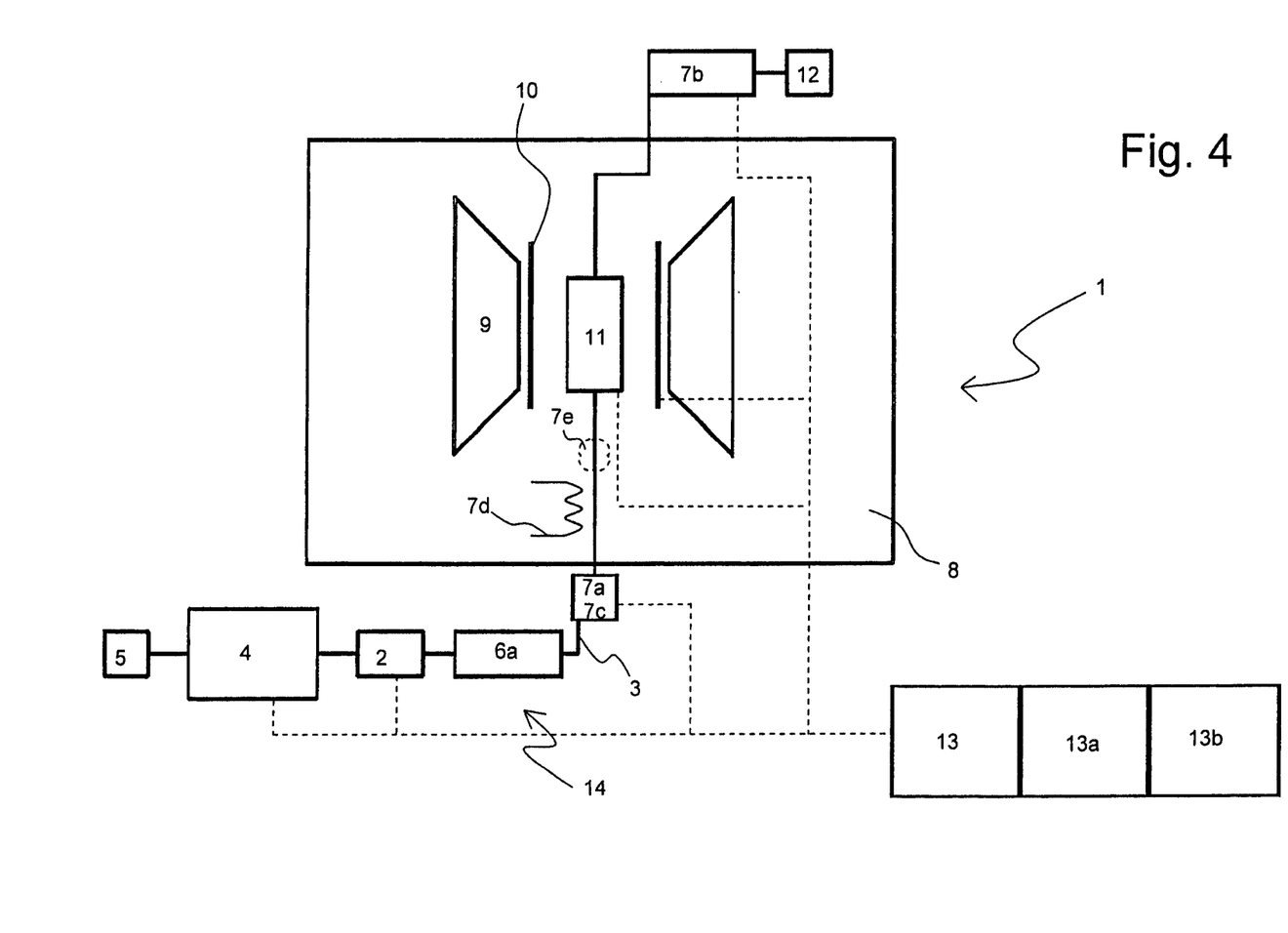
FIG. 4 A schematic overview of an inventive analysis system.

FIG. 4 shows an overview of an example of a possible embodiment of an inventive analysis system 1.

Analysis system 1 has an injector 2 with which a sample can be injected into a sample segment 3 that is connected to injector 2. In order to transport the sample, an eluent from an eluent store (solvent store) 5 is also pumped into the sample segment 3 by means of a pump 4.

The sample segment 3 contains a GPC separating column system 6a, comprising one or more parallel GPC separating columns in which the sample is separated into fractions according to size (hydrodynamic radius) based on the differing times it takes to pass through the separating column(s). The sample segment 3 then optionally passes through an analytical measuring device 7a, such as an RI detector, or, optionally through a polarization system 7c, and then finally passes into a low-field NMR spectrometer 8. The sample segment 3 or the sample transported in it can be maintained at a desired temperature by means of temperature-controlling equipment 7d (only shown schematically). Optionally, a fraction collector 7e can be installed in the flow segment.

It is important to note that parts of the chromatograph 14, for example, the separating column system 6a, the measuring equipment 7a, 7b, the polarization system 7c or the fraction collector 7e, can be disposed inside or outside the housing of the NMR spectrometer 8.

The low-field NMR spectrometer 8 comprises a permanent magnet system 9 with a shim system 10. The sample segment 3 passes through an NMR probe head 11 with a lock system (not shown in detail).

Downstream of the probe head 11, the sample segment 3 optionally passes through an analytical device 7b, such as a UV spectrometer (UV detector), and finally into a container for waste 12 (or alternatively into a further optional fraction collector).

The analysis system 1 comprises a common control unit 13 for the gel permeation chromatograph 14 and the low-field NMR spectrometer 8. The common control unit 13 controls, in particular, the pump 4, the injector 2, the shim system 10 and the probe head 11, and evaluates information from the probe head 11 and the analytical measuring equipment 7a, 7b. The control unit 13 includes a function for the experiment configuration based on a control library 13a, and a data analysis function (evaluation unit) based on a spectrum and model library 13b.

Typically, the probe head 11 (including the sample in the measuring volume inside the probe head), the permanent magnet system 9 (usually at 35-45° C.) and the GPC separating column 6 (usually at 20-80° C.) are separately temperature-controlled.

Figure 5:
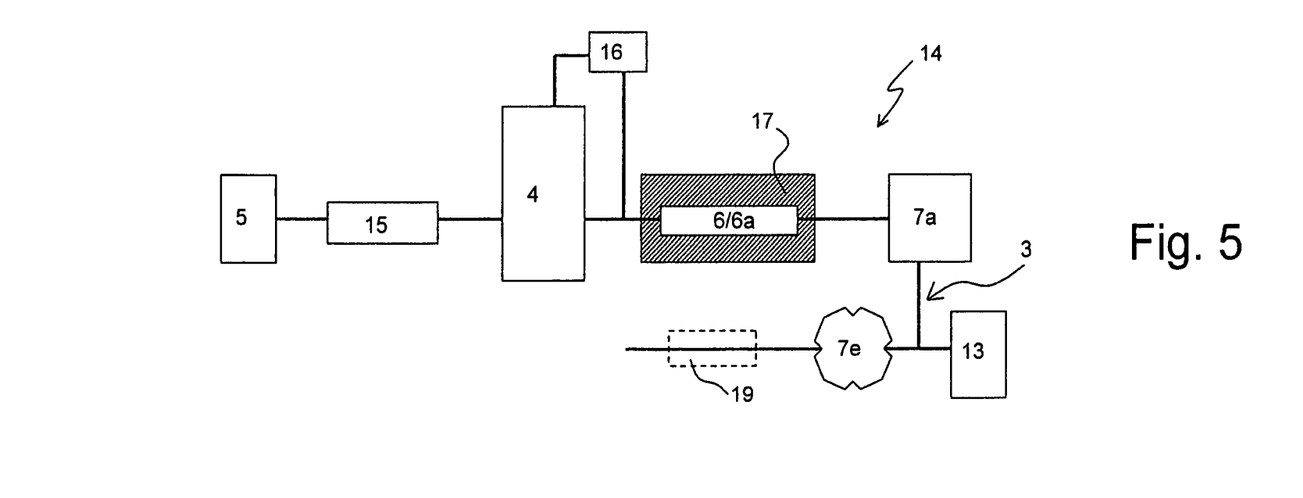
FIG. 5 A schematic overview of the GPC component of an inventive analysis system.

FIG. 5 shows an alternative embodiment of a gel permeation chromatograph 14 of an inventive analysis system in more detail. The configuration in FIG. 5 can be connected (coupled) with a low-field NMR spectrometer as shown in FIG. 4.

An eluent store (solvent store) 5 is connected to a pump 4 via a degasser 15. The pump 4 can convey both an eluent from the store 5 as well as a sample from an autosampler 16 (or from a manual injector) into a GPC separating column system 6a, in this case, comprising exactly one GPC separating column 6. The separating column 6 is surrounded by a column oven 17 for temperature-controlling the separating column 6.

The sample segment 3 then leads to an analytical measuring device (detector) 7a and finally into a fraction collector 7e, for example, a multiport valve or a loop collector. The measuring device 7a and the fraction collector 7e are connected to a control device 13. In the fraction collector 7e, the fractions that exit the separating column 6 can be isolated for a specified time by collecting the sample as it is conveyed out. The individual fractions can then be specifically conveyed into the probe head of the NMR spectrometer and measured there as long as is necessary (without being influenced by an upstream separation process).

The configuration shown in FIG. 5 can optionally be extended by an HPLC separating column 19 that is connected downstream of the fraction collector 7e. Individual collected fractions can thereby be further separated for two-dimensional chromatography.

Figure 6A:
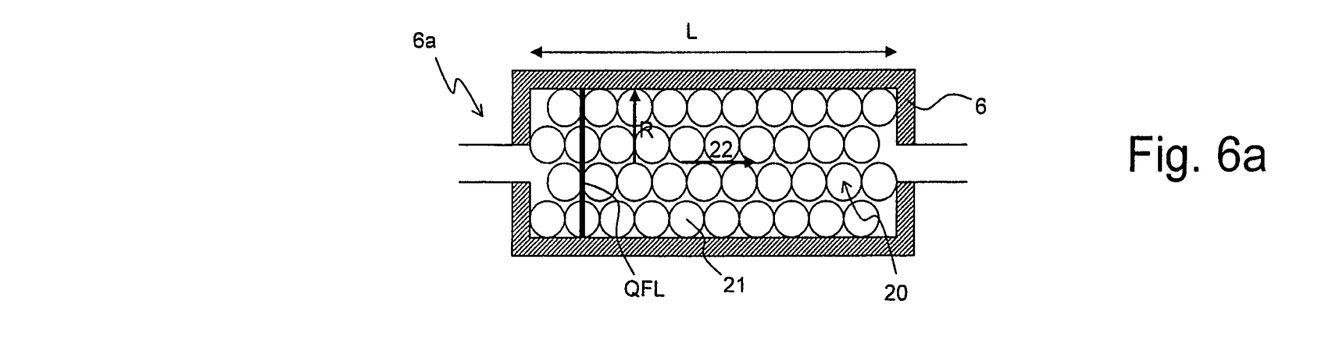
FIG. 6a A schematic view of a GPC separating column system comprising exactly one GPC separating column, for an inventive analysis system.

FIG. 6a depicts a separating column system 6a in a schematic cross-section for an inventive analysis system with only one GPC separating column 6. The separating column 6 has an interior space 20, in which porous particles 21 are disposed as a stationary phase. Molecules of the substance to be measured contained in a sample distribute themselves among the pores of the particles 21 and then diffuse out of them again. In this way, smaller particles penetrate one after the other into many pores, each requiring a certain length of time before they exit again. Larger molecules, on the other hand, have great difficulty entering the pores and are retained to a lesser degree by diffusion processes. The separating effect of the GPC is based on this entropic process.

The internal volume of the interior space 20 that at least approximates to a cylindrical shape results from the cross-section area QFL and the length L of the separating segment of the separating column 6, both with reference to the flow direction 22. According to the invention, the internal volume of the separating column is 45 cm$^3$ or larger, and the aspect ratio ASP is 5 or more, preferably 15 or more, wherein the aspect ratio is defined as ASP=L/R, with R=(QFL/$\pi$)$^{1/2}$, wherein R is the radius equivalent of the base area QFL. In the case of a circular cross-sectional area QFL, R is the radius of the circular cross-sectional area QFL.

Figure 6B:
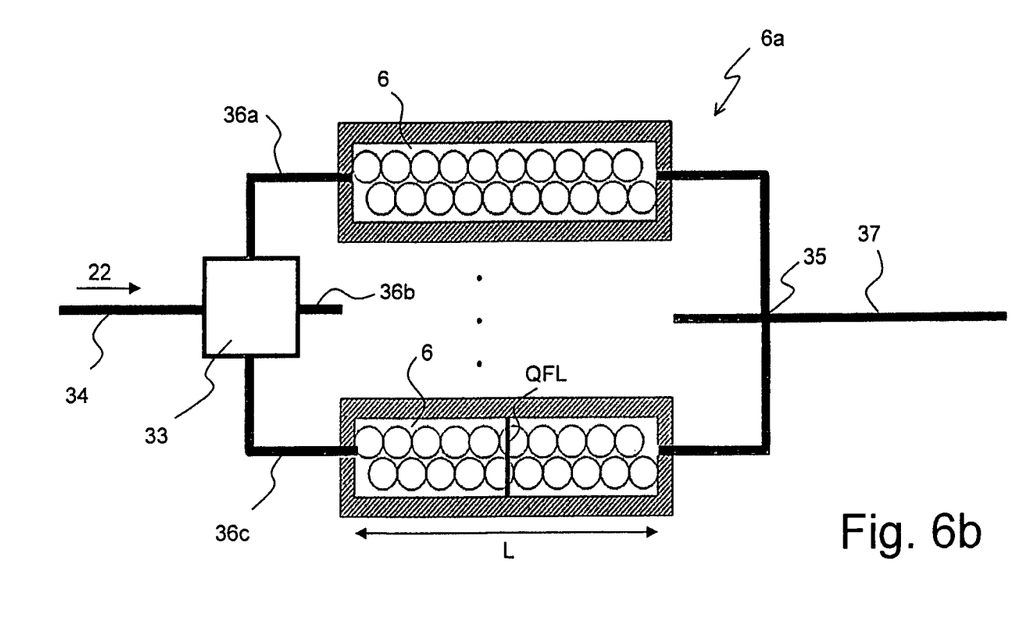
FIG. 6b A schematic view of a GPC separating column system comprising multiple GPC separating column systems connected in parallel, for an inventive analysis system.

FIG. 6b shows a GPC separating column system 6a in a schematic cross-section, comprising (here) multiple identical GPC separating columns 6.

The sample conveyed via a supply line 34 (cf. flow direction 22) is evenly distributed in a diffuser 33 across multiple branch lines 36a-c (for reasons of simplification, FIG. 6b only shows the outside branch lines 36a, 36c in full; the number N of branch lines 36a-c is typically between two and eight). A separating column 6 is disposed in each branch line 36a-c, whose interior space is filled with porous particles. The branch lines 36a-c are finally reunited again at a confluence 35, and the separated sample is conveyed further toward the NMR probe head via an outgoing line 37. The confluence 35 is preferably constituted symmetrically with respect to the branch lines 36a-c (for example, by numerical symmetry corresponding to the number N of branch lines 36a-c) to ensure a similar tube resistance in each branch line 36a-c. The fractions of the sample separated into the various separating columns 6 of the branch lines 36a-c arrive simultaneously at the confluence 35.

The pressure with which the sample and eluent is conveyed can be individually set with the diffuser 33 for each branch line 36a-c. In this way, slight differences in the flow behavior between the branch lines 36a-c (for example, a randomly different packing density of the porous articles in the separating columns 6) can be compensated for. Preferably, a variably settable delaying segment is installed in the diffuser 33 in each branch line 36a-c, so that the retention time differences between the branch lines 36a-c (for example, due to slight capillary length distances in the branch lines 36a-c) can be compensated for.

The uniform cross-sectional area QFL (perpendicular to the flow direction 22), the uniform length L of the separating segments (in flow direction 22) and the number N of identical, parallel GPC separating columns 6 are preferably selected such that an aspect ratio ASP=L/R is greater than or equal to 5, and especially preferably greater than or equal to 15, where $R=(SQFL/\pi)^{1/2}$ and SQFL=N*QFL. SQFL here designates the sum of the cross-sectional areas of all parallel GPC separating columns 6 of the separating column system 6a, and R, an associated radius equivalent.

In addition, further analytical measuring devices, in particular RI detectors can be provided in one or more branch lines 36a-c analogous to the embodiment illustrated in FIG. 4.

Figure 7:
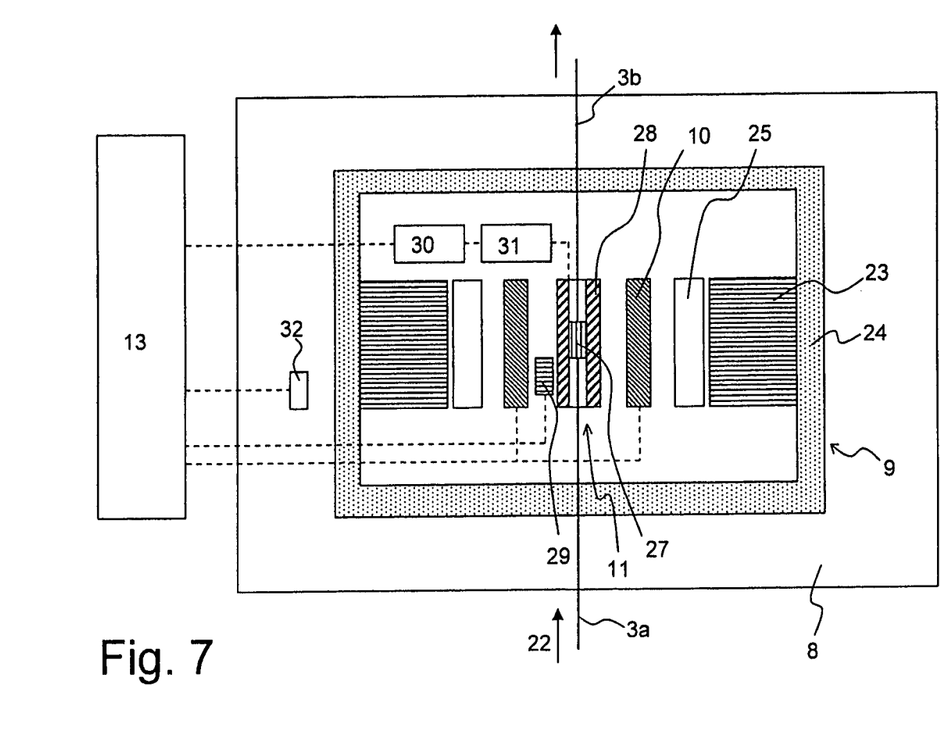
FIG. 7 A schematic view of an NMR component of an inventive analysis system.

FIG. 7 depicts an example of the region of a low-field NMR spectrometer 8 for an inventive analysis system.

The low-field NMR spectrometer 8 essentially comprises a mirror-symmetrical permanent magnet system 9 with two permanent magnets 23 that are connected by means of a yoke 24, with two pole shoes 25, and with one electric shim system 10 that is operated by a control unit 13. A homogenous static magnet field $B_0$ is generated by the permanent magnet system 9 in a sample volume 27, which here additionally functions as a measuring cell for the sample in the NMR probe head 11. It is important to note that the measuring cell can also be smaller than the homogenous sample volume 27. The sample is transported in flow direction 22 via a supply line 3a and an outgoing line 3b.

The probe head 11 (here) comprises an RF coil 28 that can radiate NMR pulses into the sample volume 27 and can detect an RF response of the sample in the sample volume 27 (alternatively, multiple RF coils can be provided, for example, for separate transmission and reception functions). The probe head 11 has a lock probe 29 in the region of the $B_0$ field with a supply line and outgoing line.

The low-field NMR spectrometer 8 further has a TX/RX switch (switches between RF irradiation and RF detection) including a pre-amplifier 30 and an optional Q switch 31. Further, temperature control of the permanent magnet system 9 with a probe 32 is provided.

The control unit 13 controls and evaluates on the NMR side, in particular, the shim system 10, the temperature control/probe 32 and the RF unit, comprising, in particular, the probe head 11 with RF coil 28, the TX/RX switch 30 and the optional Q switch 31.

To simplify the diagram, the probe head 11 is depicted rotated through 90° in FIG. 7.

Preferred Embodiment of the Magnet System

In a preferred embodiment, a permanent magnet system, like the industry standard used in the basic version of the so-called time-domain NMR or the low-resolution NMR, is used in modified form. The permanent magnet system, with magnetically active material consisting of alloys such as AlNiCo or NdBFe or SmCo, is thermally insulated and temperature-controlled (typically at 35-45° C.). The temperature control (preferably more stable than 1/100 K) stabilizes the magnetic flux, which is relatively strongly dependent on the temperature because of the material used. The temperature control produces homogeneity across the sample volume of approx. 2-10 ppm, depending on the size of the sample volume, geometry and magnetic field strength ($B_0$ field). Further measures are taken to achieve the required homogeneity of $0.5*10^{-6}$ (medium resolution). Preferably, a passive shim is inserted (for example, by optimizing and adjusting the pole shoes on the magnet). As a result, typically homogeneity of approx. 1-2 ppm is achieved. Then, preferably, an electric shim system is positioned in the free air gap (between the pole shoes). A preferred shim system has multiple-layer coil set (multi-layered copper plates) that can be individually controlled with a correspondingly dimensioned and stabilized-current power supply unit. The non-homogeneities of the magnet system can now be compensated for by the geometries selected for the various shim coils. Depending on the basic homogeneity and the orders of the non-homogeneities, a specifically optimized shim system can also be applied. A typical shim system has 8 to 12 shims (with terms 0th, 1st and 2nd order, as well as cross-terms, e.g. X, Y, Z, $Z^1$, XY, $Z^2$).

Optionally, the NMR probe head is temperature-controlled separately from the permanent magnet system; further, the GPC separating column system including the flow segment is optionally separately temperature-controlled.

Preferred Embodiment of the GPC

The following is preferred for a gel permeation chromatograph in an inventive analysis system coupled with a low-field NMR spectrometer A variable injection volume in the range of 10 µl-500 µl, typically 100 µl, A separating column with the dimensions: internal diameter of 8-40 mm, especially preferably an internal diameter of at least 20 mm, a length of 15-60 cm, alternatively multiple parallel separating columns with internal diameter dimensions of 5-30 mm, preferably at least an internal diameter of 8 mm, a length of 15-60 cm, A sample injection quantity of 20 µg-2 g, preferably at least 500 µg, especially preferably at least 2 mg, as a rule not more than 100 mg, A carrier material for the column containing particle sizes in the range 5-30 µm, and especially preferably at least 15 µm particle diameter, A concentration detector, typically RI.

The preferred pump for a GPC experiment to deformulate complex polymer blends is an isocratic (conveying identical volumes per unit of time for all back-pressures) high-performance pump for liquid chromatography. The sample dispenser can preferably be programmed and automated with respect to injection volume, injection time and number of injections ("autosampler"). Depending on the measurement task or the sample, the GPC separating column system is set up either for organic or for aqueous eluents. The detector, typically a concentration detector and preferably based on refractive index (RI) or ultraviolet (UV) measurement, can detect the separated polymers.

The sample to be analyzed (substance to be measured) is dissolved in a suitable eluent, which thus constitutes the sample, and injected into the gel permeation chromatograph by means of an autosampler. The eluent is the solvent of the sample.

The control system 13 comprises GPC analysis software to acquire and evaluate the data, which can convert the measured elugrams to the corresponding average mole mass values and mole mass distributions, taking account of a suitable calibration curve. For this, the detector values are digitized and sent to a PC equipped with the software required to process the measured data accordingly.

The GPC separating column system is defined, on the one hand, by its dimensions and the chemistry of the carrier material and, on the other hand, by the size of the particles in the column or columns and the porosity of the particles. Which carrier material is used depends on the chromatographic task. As a rule, hydrophilic polymer carrier materials with OH functionality on the surface (e.g. PSS SUPREMA), are used for aqueous applications, for example, for biopolymers, and hydrophic polymer carrier materials with aromatic or ester functionality (e.g. PSS-SDV or PSS-GRAM) are used for organic applications. The dimensions of the GPC separating column system determine the sample injection quantity.

Regarding the use of a single GPC separating column: Typically, sample quantities of 20-100 μl with a concentration of 1-3 g/l are injected into a 8×300 mm (diameter×length) separating column. The sample injection quantity is also dependent on the polydispersity $D=M_w/M_n$ of the analyzed sample. The broader the mass distribution and therefore the more polydisperse the sample, the larger the injection quantity can be. The concentration per band (if the chromatogram or elugram is divided into n equidistant bands) is decisive. The sample injection quantity can be increased by a factor of 6 or 20 in a 20×300 mm or a 40×250 mm separating column, accordingly the latter dimensions of the separating column and the corresponding volumes are preferred. As part of this invention, internal volumes of the separating volume of 200 cm$^3$ or more, or also 300 cm$^3$ or more can be used very successfully. It is important to ensure that the column diameter is not too large so that the flow rate in the case of optimum linear flow is not excessive.

If multiple parallel separating columns are also used inventively, the sample injection quantity can be increased analogously. The summated internal volumes of the parallel separating columns can therefore correspondingly be 200 cm$^3$ or more, or also 300 cm$^3$ or more.

The GPC separating column system is the "heart" of the "chromatograph." This is where the actual separation of the polymer blend takes place. The effectiveness of the separation is primarily determined by the resolution of the separating column(s) and the pore volume. The resolution in turn is defined by the pore size and the pore size distribution. The pore volume is defined by the number of pores per particle, the particle size and the packing density of the particles in the column. Besides the parameters defined for the separating column(s), separation is also influenced by the temperature at the separating column and the flow rate. Typically and depending on the task, the temperature at the separating column or columns is between 20° C. and 80° C., and the flow rate is between 0.2 ml/min and 10 ml/min. The suitable flow rate is determined by the "Van Deemter Curve" (suitable linear flow) and the mole mass of the polymers, as well as the desired dwell time of the sample in the NMR probe head.

The Preferred Control of the Analysis System

An important aspect of the invention is the direct coupling (online coupling) of the low-field NMR with the GPC process. The GPC separating column system can either be integrated, in particular modularly, into the NMR device (spectrometer), or coupled as an external device. A common software with a common user interface performs the control.

NMR experiments must be chosen that are suitable for the selected material system and the parameters of the GPC (flow parameters, column dimensions, temperature, eluent and injection quantity). This is ideally implemented via a stored control library.

The GPC-NMR coupling is preferably operated via a graphical user interface, preferably with PSS WinGPC software. This facilitates daily operation for the user and increases user acceptance. Herein, the "NMR spectrometer" is preferably configured and controlled as an "additional detector or sensor." The control operates bi-directionally, preferably via a client-server mechanism on the operating system level (e.g. Windows, communication via ActiveX or Corba). The command software, for example, PSS WinGPC, gives the NMR data acquisition software the command to acquire the data (transfer and configuration of the NMR experiment are kept separate), the NMR part of the combined device acquires the data and processes them as prescribed (e.g. automatic phase correction, zero filling, convolution with exponential functions and Fourier transform, as well as calibration of the field axis). The data or their evaluation (e.g. amplitude/integral evaluation or peak list or also the result of multivariate data evaluation) are then returned. There, the data are further evaluated (e.g. compared with a reference spectrum from a spectrum library), stored and correlated with the chromatogram, for instance, with an automatic peak search or fully automatic data evaluation facility in the PSS WinGPC software with assigned NMR spectrum (e.g.: NMR spectrum of fraction i, reliably identified as polystyrene with a content of 3%). For further evaluation and traceability, it is possible to change over to NMR spectroscopy software (e.g. TopSpin™ from Bruker). The precise triggering of the NMR experiment is ensured by previous calibration of the flow segment and by the concentration detectors.

In a further embodiment, the fractions are collected in a multiport valve and the NMR analysis is then performed with a time delay. This has the advantage that complex, multiple or long-duration, highly sensitive, or even multiple-nucleus (X nuclei, e.g. $^{13}$C, $^{19}$F) and multidimensional NMR experiments (e.g. COSY, HSQC, Indept) can be measured in stopped flow (usually overnight), so that the depth of information can be significantly increased. A combination of continuous flow and stopped flow is also possible. For this, a fraction collector can collect the samples after the first continuous flow pass and return them to the NMR spectrometer.

The Preferred NMR Method in the Inventive Analysis System

With this invention, the sensitivity of the low-field NMR spectrometer is specifically improved over conventional low-field NMR devices. Besides measures to achieve field homogenization by means of shims, in particular, digital filters and also a probe head designed for the coupled GPC can be used.

Besides NMR pulse sequences for optimizing the contrast of the spectra, for example, by observing the relaxation times, further parameters for distinguishing between polymer signals and for improving the contrast between the useful signal and the solvent signal can be applied. Besides the relaxation contrast, specific reference is made here to spectral suppression and diffusion contrast.

The low-field NMR spectrometer is such that the spectral dispersion can be adequately implemented by a sufficiently homogenous permanent magnet, so that the components of the sample can be quantified. In particular, chemical shift and J-coupling (scalar proton-proton couplings) can be adequately measured in this "medium resolution" NMR spectrometer for a quantitative substance quantity analysis, in particular of samples that contain polymer blends. The method is such that the sensitivity of the low-field NMR spectrometer and the NMR and GPC parameters used meet the requirements of quantification for a specific measuring period (preferably one minute).

The signals obtained can be quantified directly, for example, by means of the signal amplitude at the signal maximum or by integration. Another possibility is use of multivariate data analysis methods such as, for example, partial least square regression (PLS) or MCR (multivariate curve resolution). Moreover, further parameters that are of interest to material characterization can be measured, such as relaxation times or diffusion coefficients.

We claim:

1. An analysis system for the analysis of a sample, the system comprising:
   a gel permeation chromatograph having a gel permeation chromatography (=GPC) separating column system filled with porous particles, said separating column system having at least one GPC separating column, wherein GPC separating columns of said GPC separating column system have an overall combined internal volume of at least 45 cm³ or of at least 100 cm³; and a nuclear magnetic resonance (=NMR) spectrometer coupled to said chromatograph, said NMR spectrometer being configured as a low-field NMR spectrometer having a permanent magnet system for generating a $B_0$ field of said NMR spectrometer, wherein said low-field NMR spectrometer comprises a shim system with which a homogeneity of said $B_0$ field of at least 0.5 ppm or of at least 0.1 ppm is achieved in a right circular cylindrical sample volume having a diameter of at least 5 mm and a length of at least 15 mm, said low-field NMR spectrometer further comprising a lock device to compensate for a drift of said $B_0$ field.

2. The analysis system of claim 1, wherein said GPC separating column system comprises exactly one GPC separating column, said GPC separating column having an aspect ratio ASP=L/R of at least 5 or of at least 15, wherein L is a length of a separating segment of said GPC separating column in a flow direction and R is a radius equivalent of a cross-sectional area QFL of an interior space of said GPC separating column, perpendicular to a flow direction, wherein $R=(QFL/\pi)^{1/2}$.

3. The analysis system of claim 1, wherein said GPC separating column system comprises multiple GPC separating columns connected in parallel or said GPC separating columns are connected via a diffuser.

4. The analysis system of claim 1, wherein at least 25% or at least 50% of said particles in said at least one GPC separating column have a diameter of at least 15 μm or of at least 20 μm.

5. The analysis system of claim 1, wherein said low-field NMR spectrometer comprises digital data acquisition having digital filters.

6. The analysis system of claim 5, further comprising one evaluation unit for applying numerical mathematical manipulations to increase a sensitivity and/or selectivity.

7. The analysis system of claim 1, wherein the analysis system comprises a sample that contains a deuterated solvent.

8. The analysis system of claim 1, further comprising a common control unit for both said chromatograph and said low-field NMR spectrometer.

9. The analysis system of claim 8, wherein said control unit comprises a control library storing control parameters for controlling said NMR spectrometer and said chromatograph for various types of samples, for various configurations of the chromatograph and/or for various probe heads of said NMR spectrometer.

10. The analysis system of claim 1, wherein said chromatograph comprises a temperature-controllable sample segment.

11. The analysis system of claim 1, further comprising an additional analytical measuring device, a concentration detector, a refractometer, an infrared detector, an ultraviolet detector or a refractive index detector disposed in a sample segment of the analysis system between said GPC separating column system of said chromatograph and a probe head of said NMR spectrometer and/or downstream of said probe head of said NMR spectrometer.

12. The analysis system of claim 1, further comprising a polarization system disposed in or along a sample segment of said analysis system, upstream of a probe head of said NMR spectrometer.

13. The analysis system of claim 1, the analysis system further comprising an HPLC separating column.

14. The analysis system of claim 1, wherein a probe head of said NMR spectrometer is designed for a sample pressure of at least 40 bar or of at least 60 bar, exhibits an RF quality (Q factor) of at least 100 or of at least 140, exhibits a filling factor of at least 40% or of at least 60% and/or has supply lines with an internal diameter of 0.4 mm or less or of 0.25 mm.

15. The analysis system of claim 1, wherein said low-field NMR spectrometer comprises a Q switch.

16. Use of the analysis system of claim 1, for analysis of samples containing polymers or for chemical identification and quantification of repeat units of the sample in correlation with a molecular weight distribution.

17. A method for the analysis of a sample or of a sample containing polymers, the method comprising the steps of:
a) separating the sample in a gel permeation chromatograph having a GPC separating column system filled with porous particles, the GPC separating column system comprising at least one GPC separating column, wherein all GPC separating columns of the GPC separating column system have an overall combined internal volume of at least 45 cm³ or of at least 100 cm³;
b) introducing fractions of the sample into a coupled NMR spectrometer, the NMR spectrometer being configured as a low-field NMR spectrometer having a permanent magnet system generating a $B_0$ field of the NMR spectrometer, the low-field NMR spectrometer further comprising a shim system with which a homogeneity of the $B_0$ field of at least 0.5 ppm or of at least 0.1 ppm is achieved in a right circular cylindrical sample volume having a diameter of at least 5 mm and a length of at least 15 mm, the NMR spectrometer also having a lock device to compensate for a drift of the $B_0$ field; and
c) identifying a chemical content of the sample following steps a) and b).

18. The method of claim 17, wherein the GPC separating column system comprises exactly one GPC separating column, the GPC separating column having an aspect ratio ASP=L/R of at least 5 or of at least 15, wherein L is a length of a separating segment of the GPC separating column in a flow direction and R is a radius equivalent of cross-section area QFL of an interior space of the GPC separating column perpendicular to the flow direction, wherein $R=(QFL/\pi)^{1/2}$.

19. The method of claim 17, wherein the GPC separating column system comprises multiple GPC separating columns connected in parallel or comprises GPC separating columns connected via a diffuser.

20. The method of claim 17, wherein particles are used in the at least one GPC separating column having a particle size distribution in which at least 25% or at least 50% of the particles have a diameter of at least 15 μm or of at least 20 μm.

21. The method of claim 17, wherein an analysis of the sample is performed with stopped flow or in continuous flow.

22. The method of claim 17, wherein an analysis of the sample in the NMR spectrometer comprises spectral analysis and quantitative determination of $^1H$, of non-hydrogen X nuclei, of $^{13}C$ and/or of $^{19}F$.

23. The method of claim 17, wherein an analysis of the sample in the NMR spectrometer comprises application of pulse sequences for solvent suppression, relaxation filters, frequency-selective pulse sequences, gradient-assisted NMR methods, spectral resolution for analyte separation of multivariate data analysis methods PLS (partial least square regression), MCR (multivariate curve resolution), FID-DECRA (free induction decay direct exponential curve resolution) and/or multi-pulse methods for improving a S/N√t ratio or for improving a S/N√t ratio in dynamic magnetization equilibrium.

* * * * *